Figure 1:
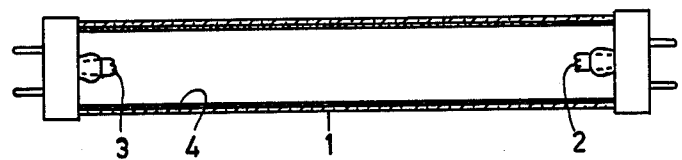

United States Patent [19]

Willemsen et al.

[11] 4,370,595
[45] Jan. 25, 1983

[54] LOW-PRESSURE MERCURY VAPOR DISCHARGE LAMP

[75] Inventors: Petrus J. M. Willemsen; Willem L. Konijnendijk; Robert C. Peters, all of Eindhoven, Netherlands

[73] Assignee: U.S. Philips Corporation, New York, N.Y.

[21] Appl. No.: 165,326

[22] Filed: Jul. 2, 1980

[30] Foreign Application Priority Data

Jul. 3, 1979 [NL] Netherlands ............... 7905162

[51] Int. Cl.³ .................. H01J 61/30; H01J 61/44
[52] U.S. Cl. ................................ 313/486; 313/493
[58] Field of Search ....................... 313/493, 486

[56] References Cited

U.S. PATENT DOCUMENTS

| 2,413,940 | 1/1947 | Bickford, Jr. | 313/487 |
| 2,447,210 | 8/1948 | Roberts | 313/486 |
| 3,581,137 | 5/1971 | Arnott et al. | 313/486 |
| 4,215,289 | 7/1980 | De Hair et al. | 313/486 |

FOREIGN PATENT DOCUMENTS 2707894 8/1978 Fed. Rep. of Germany .
1452083 10/1976 United Kingdom .
1476902 6/1977 United Kingdom .
1536637 12/1978 United Kingdom .

OTHER PUBLICATIONS

"Comparison Between Photo-Chemo-Therapy and Selective Photo-Therapy in Dermatology" by H. Tronnier et al., Article From *Afinidad*, 34, May 1977, pp. 285-290.

*Primary Examiner*—Palmer C. Demeo
*Attorney, Agent, or Firm*—Robert S. Smith

[57] ABSTRACT

Low-pressure mercury vapor discharge lamp suitable for use in photo-therapy and having a glass discharge tube which is opaque to shorter wavelength ultraviolet radiation and bears a luminescent layer on its inside surface. A problem in such lamps is to produce a useful quantity of radiation which is effective for photo-therapy in combination with as low a quantity of erythema-producing radiation as possible. The luminescent layer comprises a luminescent material having the characteristic line emission of gadolinium at 312 nm, and the glass has an absorption edge located between 280 and 305 nm.

4 Claims, 2 Drawing Figures

LOW-PRESSURE MERCURY VAPOR DISCHARGE LAMP

The invention relates to a low-pressure mercury vapor discharge lamp for radiation purposes having a discharge tube made of glass having an absorption edge between 280 and 305 nm, the tube being coated on the inside with a luminescent layer.

It is known that radiation in the wavelength range from 305-320 nm may have a favorable therapeutic effect, for example in the treatment of psoriasis and other skin diseases (see an article by H. Tronnier et al in Afinidad, May 1977, pages 285-290). A lamp of the type defined in the opening paragraph, intended to radiate selectively in the above-mentioned wavelength range is disclosed in German patent application No. 2,707,894, which has been laid open to public inspection. The known lamp is provided with a luminescent layer of a luminescent, cerium-activated strontium aluminate. Cerium-activated aluminates, which are described in Netherlands patent applications Nos. 7214862 and 7401935 (to which United Kingdom Pat. Nos. 1,452,083 and 1,476,902 correspond) have a comparatively wide emission band (half-value width approximately 45 nm) with a maximum at approximately 310 nm, so that approximately half of the radiation emitted by these materials is located in the UVB-portion of the erythema range (290-315 nm). At the maximum erythema sensitivity (approximately 297 nm) the intensity of this material is still approximately 75% of the peak value at 310 nm. As, generally, only a minute quantity of erythema radiation is permissible in photo-therapy, a filter is used in the known lamp. For this reason, the discharge tube bearing the luminescent layer is made of a glass having an absorption edge between 280 and 305 nm, that is to say the transmission curve of the glass attains a value of 10% at a wavelength in the range from 280 to 305 nm, the transmission of the glass having still lower values below that wavelength. As a result thereof the lamp emits substantially no radiation below that value and also the radiation in the range from 280 to 305 nm is limited.

The above-mentioned German Patent Application discloses such a lamp consisting of glass the transmission of which is substantially 0% at 295 nm. This lamp has the serious drawback that the quantity of useful radiation emitted is low. It appeared that for each watt of total radiation emitted in the UV (250-400 nm) range, the lamp produces only 0.14 watt of useful radiation in the range from 307.5 to 317.5 nm. Consequently, long irradiation times are necessary for photo-therapy treatments with all the drawbacks that this entails. A further drawback of the known lamp is that the quantity of erythema radiation emitted by the lamp is considerably above the minimum quantity which is theoretically possible. Since the erythema sensitivity curve (as defined by the Commission Internationale de l'Eclairage) in the range from 307.5 to 317.5 nm has values ranging from 20% to almost 0%, radiation in this wavelength range also shows erythema activity. Radiation having, for example, an equi-energy spectrum, has in this range, per watt approximately 0.08 erythema watt, which is the lowest quantity of erythema radiation which can be obtained. However, the known lamp appears to radiate approximately 0.17 erythema watt per watt of useful radiation. For a given permissible erythema load, this means a limitation of the dose of useful radiation per photo-therapy treatment and, consequently, an increase in the number of treatments required.

It is an object of the invention to provide a lamp for radiation purposes having a high useful efficiency and a significantly reduced intensity of erythema radiation.

The invention provides a low-pressure mercury vapor discharge lamp for radiation purposes having a discharge tube made of glass having an absorption edge between 280 and 305 nm, the tube being coated on the inside with a luminescent layer comprising a luminescent material which shows the characteristic line emission of gadolinium at 312 nm.

The invention is based on the recognition of the fact that a high useful efficiency combined with a low erythema load can only be obtained when very severe requirements are imposed on the luminescent material to be used. In addition to a high efficiency on excitation by 254 nm radiation, the material must have an emission which is substantially wholly concentrated in the range from 305-320 nm, substantially all the radiation emitted by the material then being useful radiation, and the amount of erythema radiation will then approach the lowest value which is theoretically possible. It appeared that materials having the characteristic line emission of gadolinium at 3.12 nm satisfy these conditions. The Gd-ion has a characteristic emission spectrum, that is to say the spectrum is only little dependent on the host lattice in which the luminescent ion is incorporated. The Gd-emission consists of a very narrow band (actually some closely adjacent emission lines) with a maximum at approximately 312 nm. The halfwidth value of this emission band is only 2 to 4 nm. Furthermore, the Gd-luminescence appears to occur very efficiently in different host lattices.

With a lamp according to the invention it is possible to obtain a high useful efficiency. Instead of the emitted radiation (of the known lamp) of only 0.14 watt of useful radiation (307.5-317.5 nm) per watt in the UV (250-400 nm) portion of the spectrum, this fraction of useful radiation is a factor of 4 to 5 higher, namely 0.50 to 0.75 watt per watt, in a lamp according to the invention. A great advantage of a lamp according to the invention is the very low fraction of erythema radiation; it appears, namely that, depending on the type of glass chosen, the erythema radiation can be limited to approximately 0.09 erythema watt for each watt of useful radiation, which value approaches the theoretically possible minimum quantity very closely.

In one embodiment of a lamp according to the invention, the luminescent layer contains a borate, activated by Gd and Bi and having a composition defined by the formula $La_{1-x-y}Gd_xBi_yB_3O_6$, wherein $0.15 \leq x$, $0.001 \leq y \leq 0.05$ and $(x+y) \leq 1$. These borates which are further described in the Netherlands Patent Application No. 7607724 (which corresponds to United Kingdom Patent No. 1,536,637), emit very efficiently the characteristic Gd-radiation. On excitation by the mercury resonance radiation having a wavelength of approximately 254 nm, quantum effiencies of 70 to 75% can be obtained with these materials.

In another embodiment of a lamp according to the invention, the luminescent layer contains a ternary aluminate activated by Gd and Pb and having a hexagonal magneto-plumbite structure, the aluminate having the composition ABC, wherein A represents from 25-99 mole %$\frac{1}{2}$Gd$_2$O$_3$, 1-35 mole% PbO and, possibly $\frac{1}{2}$La$_2$O$_3$, wherein B represents Al$_2$O$_3$, not more than 20 mole % of the Al$_2$O$_3$ having been replaced by Sc$_2$O$_3$, and wherein C represents MgO and/or ZnO, up to 10 mole % of the $Al_2O_3$ possibly having been replaced by an equivalent quantity of $SiO_2$ together with MgO and/or ZnO, up to 70 mole % of A possibly having been replaced by SrO and/or CaO and, simultaneously, an equivalent quantity of C by $\frac{1}{2}$ $Al_2O_3$, and wherein the contents A, B and C satisfy the conditions $[A] \geq 0.02$, $0.55 \leq [B] \leq 0.95$ and $[C] \geq \frac{1}{2}[A]$. These luminescent aluminates are further described in the Netherlands patent application No. 7811436 which has not yet been laid open to public inspection, and appear to have high quantum efficiencies. The materials defined by the formula $Gd_{0.90}Pb_{0.15}MgAl_{11}O_{19}$ and $Gd_{0.88}Pb_{0.18}ZnAl_{11}O_{19}$, for example, have a quantum efficiency (254 nm-excitation) of 50 to 55%.

In another embodiment of a lamp according to the invention the luminescent layer contains a silicate activated by Gd and Pb, of Sr and/or Ca and of Y and/or La and has a composition defined by the formula $(Sr,Ca)_{3-p}Pb_p(Y,La)_{2-q}Gd_qSi_6O_{18}$, wherein $0.01 \leq p \leq 0.50$ and $0.05 \leq q \leq 2.0$. At 254 nm-excitation, these silicates have a quantum efficiency for the Gd luminescence of approximately 60%.

It is advantageous to choose a glass having an absorption edge between 295 and 305 nm for the discharge tube of a lamp according to the invention. Very low values are then obtained for the erythema load, as the radiation of the mercury lines at 297 and 303 nm generated in the discharge are substantially fully absorbed by this glass.

Preference is given to such lamps the glass of which contains

60–75 mole % $SiO_2$,
10–25 mole % of at least one alkali metal oxide,
7–15 mole % of at least one alkaline earth metal oxide,
0–2 mole % $Al_2O_3$
0,01–0,1 mole % $Fe_2O_3$,
0–1 mole % $(As_2O_3+Sb_2O_3)$.

These glasses, which may optionally contain small quantities (from 0–1 mole %) of a refining agent such as $Sb_2O_3$ and $As_2O_3$, have the considerable advantage of being cheap, as they are used in large quantities for low-pressure mercury vapor discharge lamps for general lighting purposes.

Figure 2:
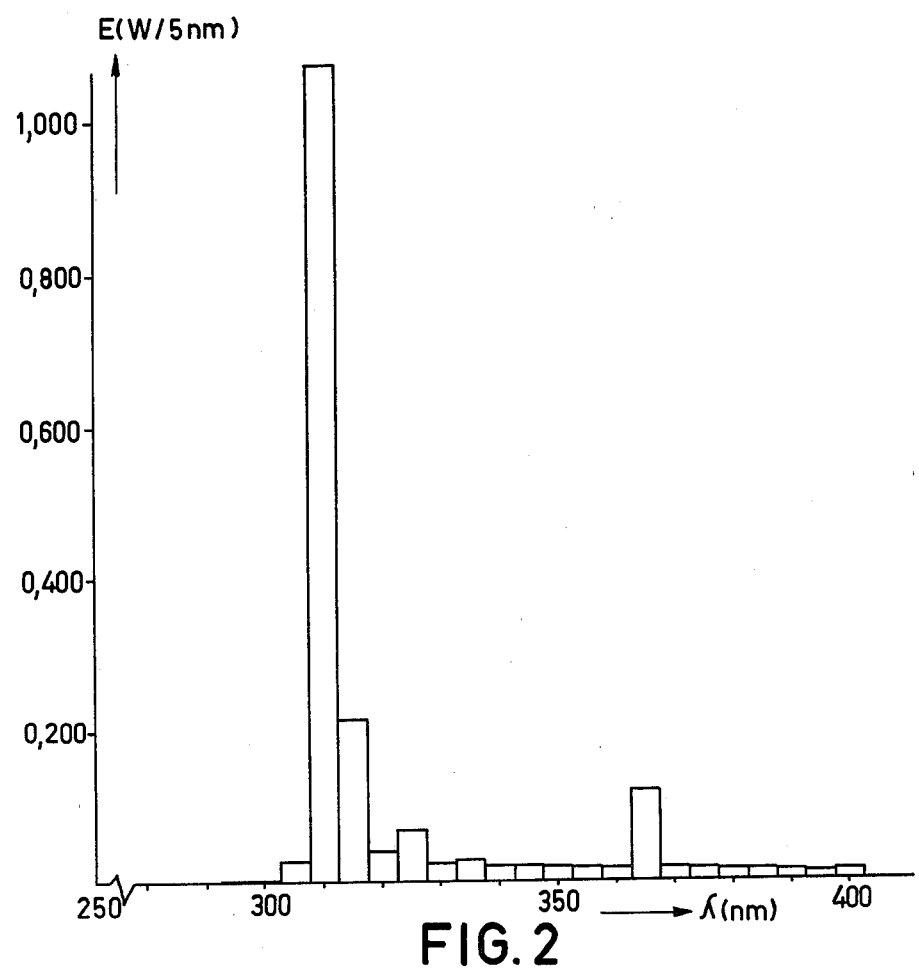

Some embodiments of lamps according to the invention will now be described with reference to the following Examples and to the drawing, in which:

FIG. 1 is a schematic longitudinal section of a lamp according to the invention and FIG. 2 shows by means of a graph the spectral energy distribution of the emitted radiation of such a lamp.

The lamp shown in FIG. 1 has a glass discharge tube 1 which is approximately 1200 nm long and has an outside diameter of approximately 38 nm. The wall thickness of the tube 1 is approximately 0.75 mm, and the glass has the following composition:
66.30 mole % (72.6% by weight) $SiO_2$,
21.96 mole % (16.9% by weight) $Na_2O$,
0.685 mole % (0.8% by weight) $K_2O$,
4.44 mole % (5.3% by weight) CaO,
5.19 mole % (2.6% by weight) MgO,
1.34 mole % (1.7% by weight) $Al_2O_3$,
0.075 mole % (0.15% by weight) $Fe_2O_3$, At approximately 304 nm this glass has a transmission of 10%. Electrodes 2 and 3 are provided, one at each end of the lamp, the discharge taking place during operation between these electrodes. The lamp contains a mixture of rare gases as the starting gas, and a small quantity of mercury. On the inside the tube 1 is coated with a luminescent layer 4, comprising a luminescent material which emits the characteristic 312 nm radiation of Gd. The layer 4 can be applied in a customary manner to the tube 1, for example by means of a suspension containing the luminescent material. During operation the lamp consumes a power of 40 W.

EXAMPLE 1

A number of lamps of the type described with reference to FIG. 1 were coated with a layer of luminescent borate having a composition defined by the formula $La_{0.487}Gd_{0.5}Bi_{0.013}B_3O_6$. After having been in operation for 100 hours, it appeared that these lamps emitted over the whole UV spectrum (from 250–400 nm) a quantity of radiation totaling 1.800 W. The quantity of useful radiation in the range from 307.5 to 317.5 nm appeared to be 1.290 W, that is to say approximately 72% of the total emitted radiation is useful radiation. FIG. 2 is a graphical representation of the spectral energy distribution of the radiation emitted by this lamp. The wavelength $\lambda$ in nm is plotted on the horizontal axis, the emitted radiant energy E being plotted on the vertical axis in W per wavelength interval of 5 nm.

EXAMPLE 2

Lamps having a construction as described with reference to FIG. 1 but having a 1500 nm long tube and intended to consume a power of 80 W, were coated with a luminescent layer of the same luminescent material as was used in Example 1. After having been in operation for 100 hours, a total UV (250–400 nm) emitted quantity of radiation of 2.75 W was measured on these lamps. It appeared that 1.46 W (that is to say approximately 53%) was emitted in the range from 307.5–317.5 nm. The quantity of erythema radiation emitted by the lamp appeared to be 0.14 erythema watt, that is to say only approximately 9.6% of the total quantity of useful radiation. For comparison, the known lamps having a construction similar to the lamps described above but made of glass containing a luminescent cerium-activated strontium aluminate, emit in total (250–400 nm) a radiation of 5.9 W. However, only approximately 14% (0.83 W) of this quantity of radiation is located in the range from 307.5–317.5 nm. In addition, it appeared that the quantity of erythema radiation emitted by the known lamp was 16.7% of the quantity of useful radiation (namely approximately 0.14 erythema watt). When the lamps according to the invention are used, it is therefore possible, in order to obtain the same quantity of useful radiation as that emitted by one of the said known lamps, to reduce the radiation time by more than 40%, while the erythema dose is reduced by approximately the same percentage.

EXAMPLE 3

A number of lamps of the type shown in FIG. 1 were made using a luminescent layer comprising a luminescent silicate having a composition defined by the formula $Sr_{2.9}Pb_{0.1}LaGdSi_6O_{18}$. After having been in operation for 100 hours a quantity of radiation of 1.25 W, emitted over the whole ultra-violet portion (250–400 nm) of the spectrum was measured on these lamps. It appeared that 0.9 W thereof was emitted in the range from 307.5 to 317.5 nm. It appeared that for these lamps the spectral energy distribution of the emitted radiation was substantially equal to those of the lamps described in Example 1.

What is claimed is:

1. A low-pressure mercury vapor discharge lamp for radiation purposes having a discharge tube made of glass having an absorption edge between 280 and 305 nm, the tube being coated on the inside with a luminescent layer comprising a luminescent material which has the characteristic line emmission of gadolinium at 312 nm, the luminescent layer comprises a borate activated by Gd and Bi, this borate having a composition defined by the formula $La_{1-x-y}Gd_xBi_yB_3O_6$, wherein 0.15 is less than or equal to x, 0.001 is less than or equal to y which is less than or equal to 0.05 and (x+y) is less than or equal to 1, the luminescent layer containing a ternary aluminate activated by Gd and Pb and having the hexagonal magneto-plumbite structure, the aluminate having the composition ABC, wherein A represents from 25–99 mole % ½ $Gd_2O_3$, 1–35 mole % PbO and, up to ½ $La_2O_3$, wherein B represents $Al_2O_3$, not more than 20 mole % of the $Al_2O_3$ being replaceable by $Sc_2O_3$ and wherein C represents a material selected from the group consisting of MgO and ZnO, up to 10 mole % of the $Al_2O_3$ possibly being replaceable by an equivalent quantity of $SiO_2$ together with at least a compound selected from the group consisting of MgO and ZnO, up to 70 mole % of A being replaceable by a compound selected from the group consisting of SrO and CaO, simultaneously, an amount of C equivalent to the amount of B replaced, being replaceable by ½ $Al_2O_3$, A, B and C satisfying the conditions [A] is greater than or equal to 0.02, 0.55 is less than or equal to [B] which is less than or equal to 0.95 and [C] is greater than or equal to ½ A.

2. A low-pressure mercury vapor discharge lamp as claimed in claim 1, characterized in that the luminescent layer comprises a Gd and Pb-activated silicate of Sr and/or Ca and of Y and/or La having a composition defined by the formula $(Sr,Ca)_{3-p}Pb_p(Y,La)_{2-q}Gd_qSi_6O_{18}$, wherein 0.01 is less than or equal to p which is less than or equal to 0.50 and 0.05 is less than or equal to q which is less than or equal to 2.0.

3. A low-pressure mercury vapor discharge lamp as claimed in claim 1 or 2, characterized in that the glass of the discharge tube has an absorption edge between 295 and 305 nm.

4. A low-pressure mercury vapor discharge lamp as claimed in claim 3, characterized in that the glass of the discharge tube consists of the following constituents in the specified quantities:

60–75 mole % $SiO_2$,
10–25 mole % of at least one alkali metal oxide,
7–15 mole % of at least one alkaline earth metal oxide,
0–2 mole % $Al_2O_3$,
0.01–0.1 mole % $Fe_2O_3$, and
0–1 mole % $(As_2O_3+S_bO_3)$.

* * * * *